(12) United States Patent
Jung et al.

(10) Patent No.: US 6,682,782 B2
(45) Date of Patent: Jan. 27, 2004

(54) ORGANIC COMPOUND HAVING AN ACETYLENE GROUP, VACUUM DEPOSITION POLYMERIZATION THEREOF, DEPOSITED POLYMERIZED THIN FILM, AND ELECTROLUMINESCENCE DEVICE CONTAINING SAME

(75) Inventors: Sang Hyun Jung, Taean-kun (KR); Chang Jin Lee, Yusung-ku (KR); Yong Ku Kang, Shinsung-dong (KR); Sung Koo Lee, Bundang-ku (KR); Hee Jung Kim, Myungjang-dong (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 121 days.

(21) Appl. No.: 09/752,555

(22) Filed: Jan. 3, 2001

(65) Prior Publication Data

US 2002/0018912 A1 Feb. 14, 2002

(30) Foreign Application Priority Data

Jul. 3, 2000 (KR) .......................................... 2000-37784

(51) Int. Cl.[7] .............................................. C23C 14/06
(52) U.S. Cl. ........................ 427/497; 427/509; 427/558; 427/255.6; 427/384; 427/69
(58) Field of Search ................................. 427/497, 509, 427/558, 255.6, 384, 69

(56) References Cited

FOREIGN PATENT DOCUMENTS

| JP | 08-020650 | * | 1/1996 |
| WO | 98/28767 | * | 7/1998 |

OTHER PUBLICATIONS

Greiner, A., "Poly(1,4–xylylene)s: Polymer Films by Chemical Vapour Deposition", Trends in Polymer Science, vol. 5, No. 1, Jan. 1997.

Smith, D.W., et al., "Polynaphthalene Networks from Bisphenols", J. Am. Chem. Soc. 1998, 120, 9078–9079.

Vaeth, V.M., et al., "Poly(p–phenylene vinylene) Prepared by Chemical Vapor Deposition: Influence of Monomer Selection and Reaction Conditions on Film Composition and Luminescence Properties", Macromolecules 1998, 31, 6789–6793.

Nason, T.C., et al., "Deposition of Amorphous Fluoropolymer Thin Films by Thermolysis of Teflon Amorphous Fluoropolymer", Appl. Phys. Lett., 60 (1992), 1866–1868.

Ukishima, S., et al., "Heat Resistant Polyimide Films with Low Dielectric Constant by Vapor Deposition Polymerization", Thin Solid Films, 308–309 (1997), 475–479.

Kubono, A., et al., "In–situ Study on Alternating Vapor Deposition Polymerization of Alkyl Polyamide with Normal Molecular Orientation", Thin Solid Films, 289 (1996), 107–111.

Fukuda, F., "Pyroelectricity and Piezoelectricity of Polyurea", Key Engineering Materials, 92–93 (1994), 143–160.

Tatsuura, S., et al., "Polyazomethine Conjugated Polymer Film with Second Order Nonlinear Optical Properties Fabricated by Electric–field–assisted Chemical Vapor Deposition", Appl. Phys. Lett., 62 (1993), 2182–2184.

* cited by examiner

*Primary Examiner*—Timothy Meeks
(74) *Attorney, Agent, or Firm*—Fitzpatrick, Cella, Harper & Scinto

(57) ABSTRACT

The present invention relates to an organic compound having acetylene group(s), a thin film formed by vacuum deposition polymerization using said organic compound, vacuum deposition polymerization to form said thin film, and an electroluminescence device containing said thin film. More particularly, the present invention relates to an organic compound having at least one acetylene groups, vacuum deposition polymerization in which said organic compound is deposited on the substrate and simultaneously or then polymerized by heat treatment or UV irradiation to form a polymer thin film, and an electroluminescence device using at least one layer of said thin film.

3 Claims, 11 Drawing Sheets

[Fig.2]

| Metal electrode |
| Electron transport layer |
| Emission layer |
| Hole transport layer |
| ITO electrode |

| Metal electrode |
| Emission layer |
| Hole transport layer |
| ITO electrode |

| Metal electrode |
| Emission layer |
| ITO electrode |

[Fig. 5]

ORGANIC COMPOUND HAVING AN
ACETYLENE GROUP, VACUUM
DEPOSITION POLYMERIZATION THEREOF,
DEPOSITED POLYMERIZED THIN FILM,
AND ELECTROLUMINESCENCE DEVICE
CONTAINING SAME

BACKGROUND OF THE INVENTION

Field of the Invention

The present invention relates to an organic compound having acetylene group(s), a thin film formed by vacuum deposition polymerization using said organic compound, vacuum deposition polymerization to form said thin film, and an electroluminescence device containing said thin film. More particularly, the present invention relates to an organic compound having at least one acetylene groups, vacuum deposition polymerization in which said organic compound is deposited on the substrate and simultaneously or then polymerized by thermal and/or UV radiation curing to form a polymer thin film, and an electroluminescence device using at least one layer of said thin film.

Organic functional thin film is recently used in Thin Film Transistor-Liquid Crystal Device (TFT-LCD), organic polymer electroluminescence devices, piezoelectric devices, optical materials and the like because it is applicable for portable electronics. Conventional organic thin film can be prepared by wet process such as dip coating or spin coating but it has disadvantages in that a certain polymer which is insoluble in a solvent requires an additional process of coating a precursor and heating to form a thin film. Further, wet process. results in problems including easy contamination by a solvent, difficulty in controlling film thickness and film uniformity below 100 nm. Also wet process is not favorable for a following process such as a manufacturing process of semiconductors which requires dry process.

On the other hand, a deposition polymerization is a method to produce an organic thin film by direct polymerization on the substrate by vaporizing a precursor with heat energy under high vacuum. Said deposition polymerization can i)produce a thin film through a simple vacuum device without using a catalyst or a solvent, ii)prevent from contamination of impurities, iii)control molecular sequences and film thickness, iv)provide easy preparing of a thin film of inprocessible polymer, and v)form a pattern by using a mask. Therefore, it is very important to develop thin film forming, technology by vacuum deposition polymerization which is expected to be essential to various electronic devices in future information industries.

There are two types of deposition polymerizations to form a thin film which are radical deposition polymerization and condensation polymerization. Radical deposition polymerization is a method to prepare a thin film on the substrate by polymerizing radicals generated by chemical reactions of precursors by thermal and/or UV radiation after vaporizing precursors. Different thin films such as poly(p-xylylene) (A. Greiner, Trends in Polymer 5(1997)7), 12), poly (naphthalene) (D. W. Smith et al., J. Am. Chem. Soc., 120(1998), 9078), poly(benzocyclobutene) or poly(p-phenylenevinylene) (K. M. Vaeth et al. Macromolecules, 31(1998), 6789), and Teflon (T. C. Nason et al., Appl. Phys. Lett. 60(1992), 1866), are prepared by radical deposition polymerization. Thin films prepared by said radical deposition polymerization provide excellent thermal stability and low dielectric constant and thus, they are very attractive for applications as interlayer dielectrics of semiconductors.

On the other hand, condensation polymerization is a method to prepare a thin film by condensation polymerization after two kinds of precursors are simultaneously deposited on the substrate. Thin films such as polyimide (Ukishima et al., Thin Solid Films, 308–309(1997), 479), polyamide (A. Kubono et. al., Thin Solid Films, 289(1996), 107), and polyurea (F. Fukuda, Key Eng. Mater., 92–93 (1994), 143), polyazomethane (S. Tatsuura et al., Appl. Phys. Lett., 62(1993), 2182), are prepared by condensation polymerization. Thin films prepared by said condensation polymerization provide excellent electrical and optical properties such as piezoelectricity, non-linear optical property and conductivity and thus, they call the high attention as high-functional materials.

However, said radical deposition polymerization has to generate radicals by decomposing precursors at a high temperature over 400° C. which is not suitable for the device manufacturing process. And said condensation polymerization has also disadvantages for producing by-products during condensation polymerization. Therefore, it is urgent to develop vacuum deposition polymerization which does not require thermal curing at a high temperature for decomposing precursors as well as does not produce by-products during polymerization and further, an appropriate precursor for vacuum deposition polymerization.

SUMMARY OF THE INVENTION

An object of the present invention is to provide an organic compound having at least one acetylene group which can be easily polymerized by thermal curing at relatively low temperature or UV irradiation.

Another object of the present invention is to provide a vacuum deposition polymerization to obtain a thin film having uniform thickness without generating by-products by using said organic compound.

Another object of the present invention is to provide a thin film prepared by vacuum deposition polymerization having an improved thermal stability.

Another object of the present invention is to provide an electroluminescent device fabricated by using said thin film.

BRIEF DESCRIPTION OF THE DRAWINGS

FIG. 2 represents a schematic view of electroluminescence device.

DETAILED DESCRIPTION OF THE INVENTION

The present invention is described in detail as set forth hereunder.

Organic compounds having acetylene groups of the present invention is represented in the following formula 1, $$[R_1 \text{---} \equiv \text{---} R_2]_n \text{---} R \tag{1}$$

wherein $R_1$ is a hydrogen atom or

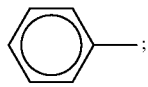

$R_2$ is bond or

n is a natural number of 1 or above; and R is selected from the group consisting of

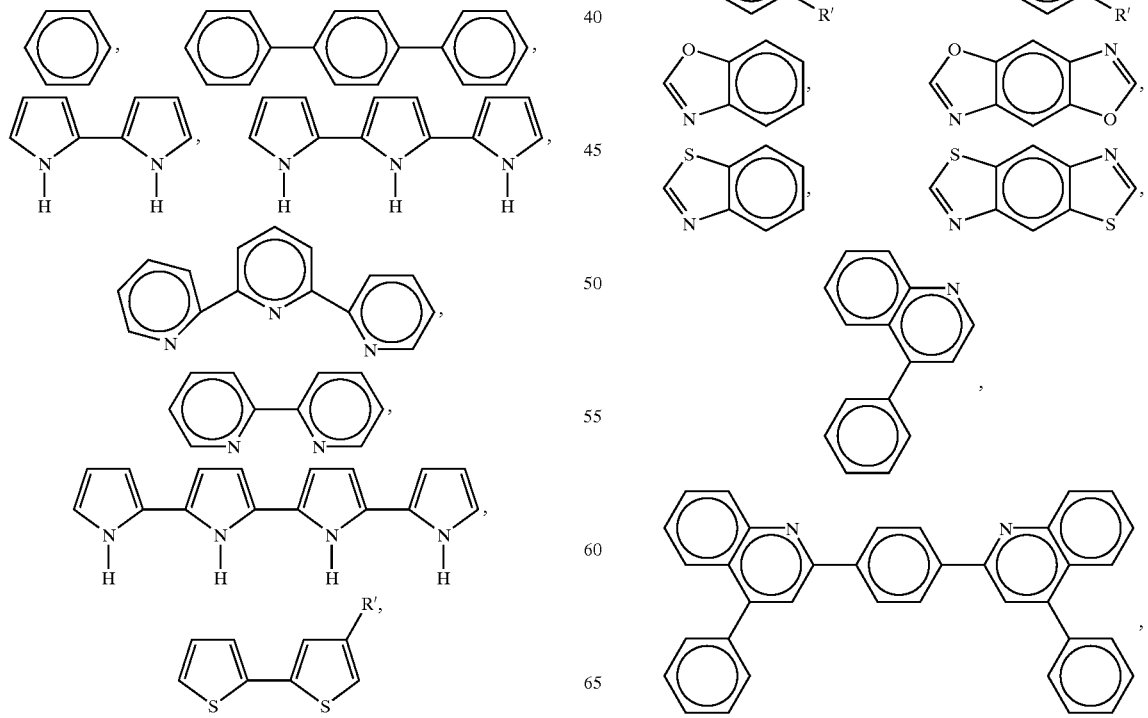

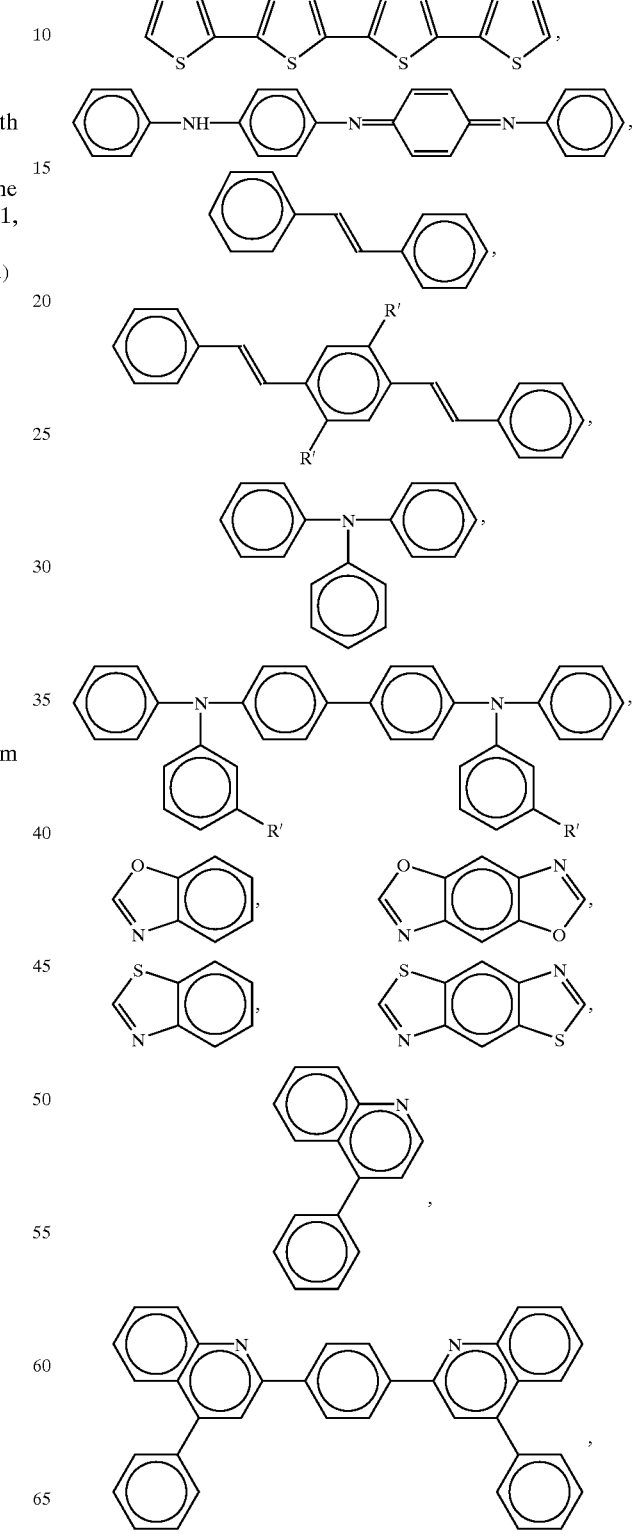

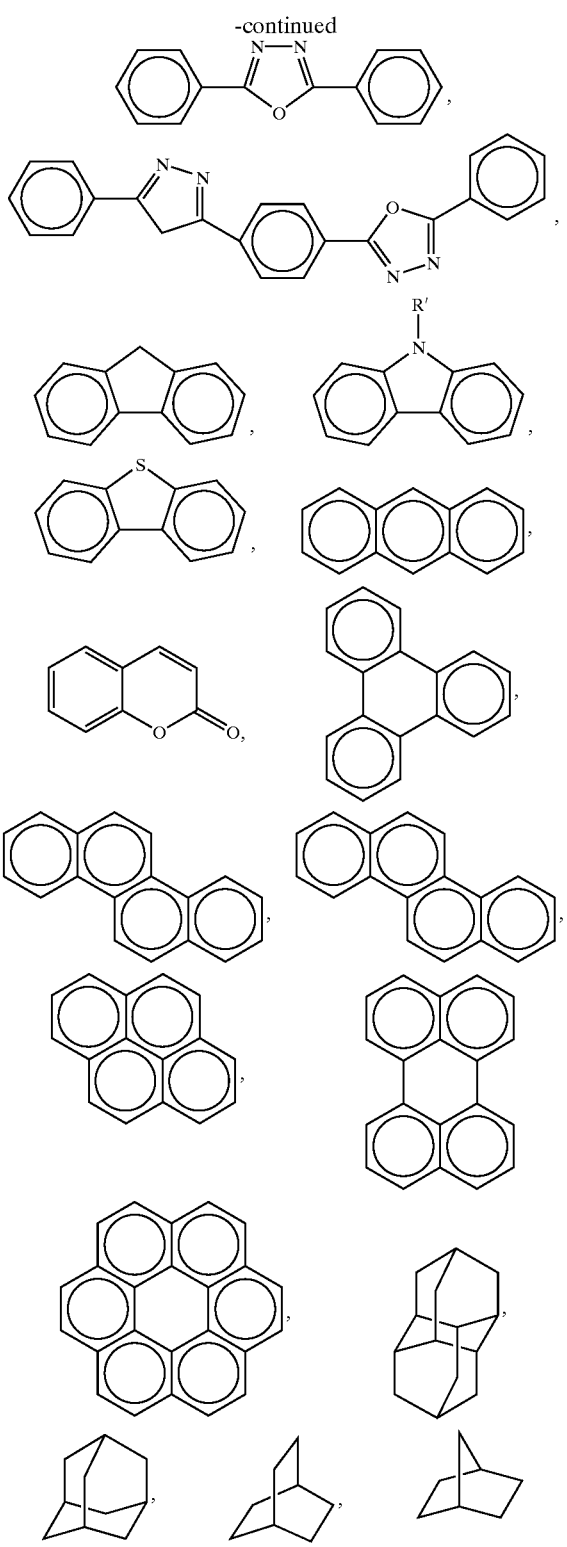

where R' is selected from the group consisting of a hydrogen atom and $C_1$–$C_{12}$ hydrocarbons.

Generally, as shown in scheme 1, an aromatic compound having acetylene group(s) is prepared by removal of trimethylsilyl group of an aromatic compound substituted with trimethylsilyl acetylene in the presence of a base or fluoro ion where said aromatic compound substituted with trimethylsilyl acetylene is prepared by reacting aryl iodide (ArI) or aryl bromide (ArBr) with trimethylsilyl acetylene in the presence of palladium catalyst.

Scheme 1

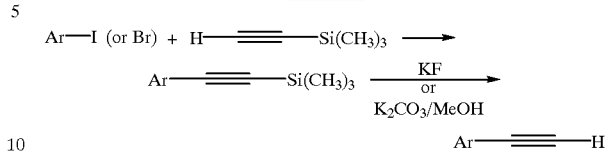

Most of compounds of formula 1 can be easily prepared from mono, di, tri, or tetra bromo (or iodo) compounds as shown in Scheme 1.

Because the compound of formula 1 having acetylene group(s) is easily cured (or polymerized) by heat treatment or UV radiation, deposition and thermal or UV radiation curing can be performed simultaneously or thermal or UV radiation curing can be performed after deposition in a process for preparing organic thin film by vacuum deposition polymerization.

Figure 1:
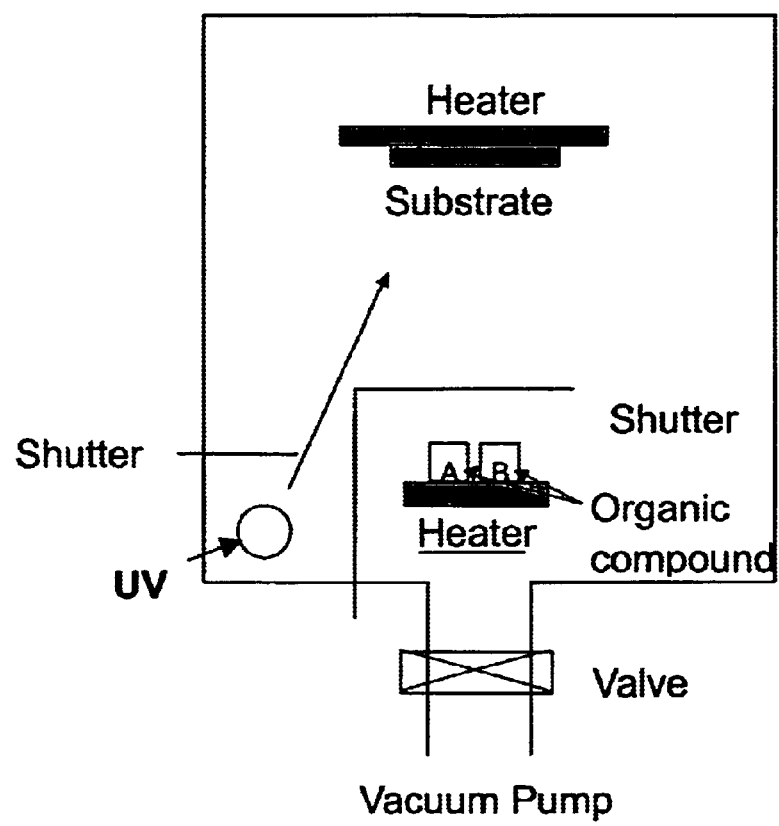
FIG. 1 represents a schematic view of vacuum deposition chamber for thermal and UV radiation curing.

Therefore, in vacuum deposition polymerization of the compound of formula 1 to prepare a polymer thin film on the substrate such as glass or silicon wafer by using vacuum deposition chamber, said polymer thin film can be prepared by deposition and simultaneous polymerization by heat treatment or UV irradiation or by deposition and then polymerization. If necessary, thermal curing can be performed again after UV irradiation to complete polymerization. FIG. 1 represents a vacuum deposition chamber which is used for deposition polymerization. Because the vacuum deposition chamber is equipped with a heater and a UV lamp for direct heating, a thin film of an organic compound can be obtained by simultaneous deposition and polymerization or sequential deposition and polymerization. It is also possible to deposit simultaneously more than two organic compounds with this vacuum deposition chamber.

In the formation of a polymer by exposing UV light according to the present invention, pattern can be easily formed by using a mask. The only exposed area through the mask can be cured and the unexposed area is removed under the vacuum or by dissolving in a solvent so that it is possible to form the pattern wanted.

The thin film formed by vacuum deposition polymerization of the present invention provides improved thermal stability and thus, it can be applied in various fields such as interlayer dielectrics of semiconductors, hole transport layer and emission layer of electroluminescence device, solar cells, drum of copy machine and laser printer, and various sensors.

As shown in FIG. 2 which represents an electroluminescence device prepared by using deposition polymerized thin film, it basically includes ITO electrode, emission layer and metal electrode. Said emission layer is a thin film prepared by means of vacuum deposition polymerization of the compound of formula 1 having at least one acetylene group. An electroluminescence device can have a hole transport layer under an emission layer. At least either a hole transport layer or an emission layer can be prepared by vacuum deposition polymerization of the present invention. And further, an electroluminescence device can, additionally, have an electron transport layer on the emission layer. Among an emission layer, a hole transport layer and an electron transport layer, at least one layer is prepared by vacuum deposition polymerization of the present invention.

EXAMPLE 1

Preparation of 2-Ethynylfluorene

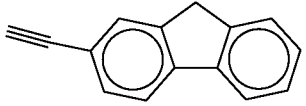 (1)

10 g (0.06 mol) of fluorene and 15.23 g (0.06 mol) of iodine were added into 300 ml of acetic acid and stirred. 1.2 ml of nitric acid and 12 ml of sulfuric acid were added dropwise into the reaction mixture. After the reaction mixture was stirred 35° C. for 2 h, 2L of distilled water was added to it. Unreacted fluorene was washed out with 100 ml of cold acetic acid. Remaining precipitates were washed with 100 ml of 5% potassium iodide solution, 100 ml of 5% sodium thiosulfate solution and distilled water, successively. Washed precipitates were dried in the air and extracted by petroleum ether soxhlet. Extracted solution was cooled to obtain 7.89 g (45%) of yellow needle shape 2-iodofluorene.

Thereafter, to 150 ml of trimethylamine were added 7.89 g of 2-iodofluorene, 379 mg (0.54 mmol) of bis[triphenylphosphine]palladium dichloride and 51 mg (0.27 mmol) of copper iodide. 4.2 ml (29.7 mmol) of trimethylsilylacetylene was added slowly to the reaction mixture. After the reaction was stirred for 8 h at room temperature, solvent was removed under reduced pressure. The residue was extracted with benzene and the benzene layer was washed with distilled water. The washed benzene layer was concentrated to give 6.02 g (85%) of 2-trimethylsilylethynyl fluorene.

Figure 3:
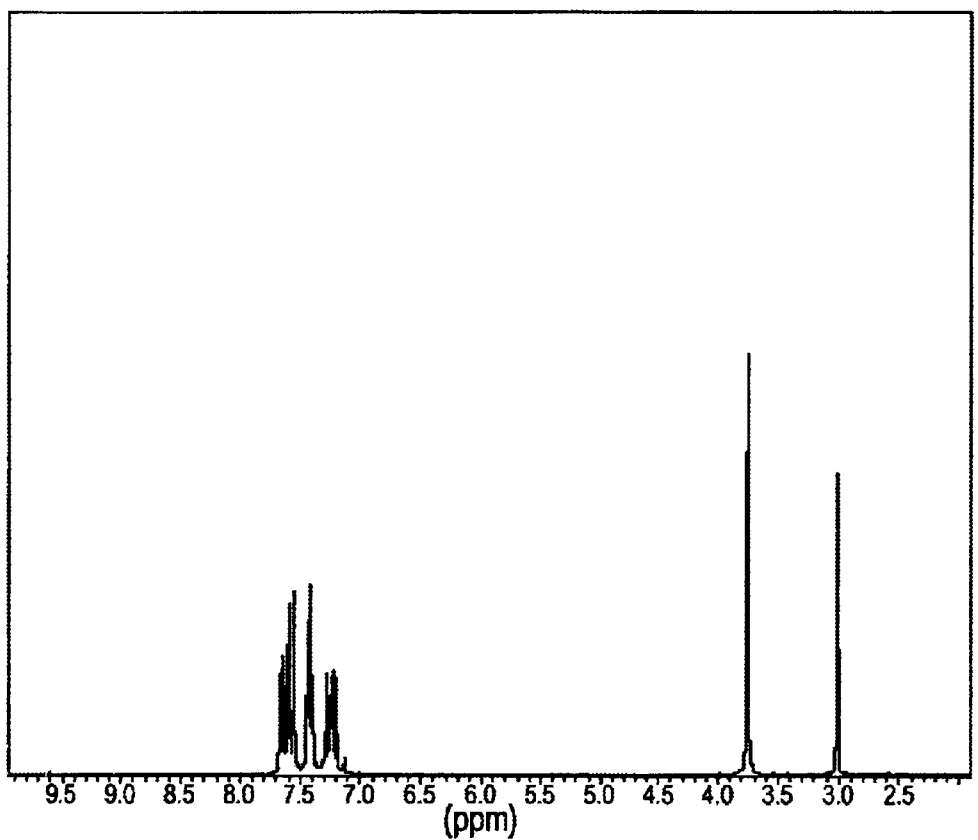
FIG. 3 represents NMR spectrum of 2-ethynylfluorene.

After 6.02 g (22.9 mmol) of 2-trimethylsilylethynylfluorene was added to 100 ml of methanol, 25 ml of 1N potassium hydroxide was added dropwise thereto. The reaction mixture was stirred for 3 h at room temperature and solvent was removed under the reduced pressure. The residue was extracted with ether and the ether layer was washed with distilled water. The washed ether layer was dried over anhydrous sodium sulfate and concentrated under the reduced pressure to give crude product. The crude product was purified by column chromatography on silica gel by eluting hexane/ethylacetate(15/1) and further purified by sublimation at 60° C./2torr to give 3.71 g (87%) of 2-ethynylfluorene. FIG. 3 represents NMR spectrum of the final product, 2-ethynylfluorene, and mp was measured to be 85° C.

Figure 4:
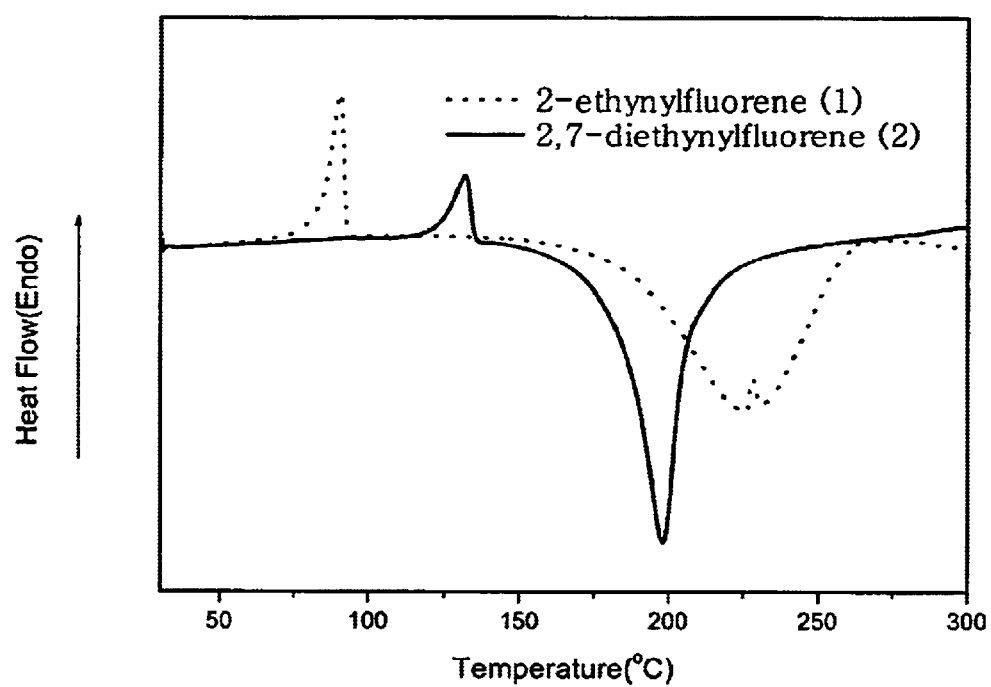
FIG. 4 represents DSC thermograms of 2-ethynylfluorene and 2,7-diethynylfluorene.

The DSC thermogram of 2-ethynyl fluorene as shown in FIG. 4 reveals that polymerization of 2-ethynyl fluorene having one acetylene group was started at around 230° C. It indicated that deposition on the substrate and polymerization of 2-ethynylfluorene can be performed simultaneously by controlling a temperature at 230° C.

Figure 5:
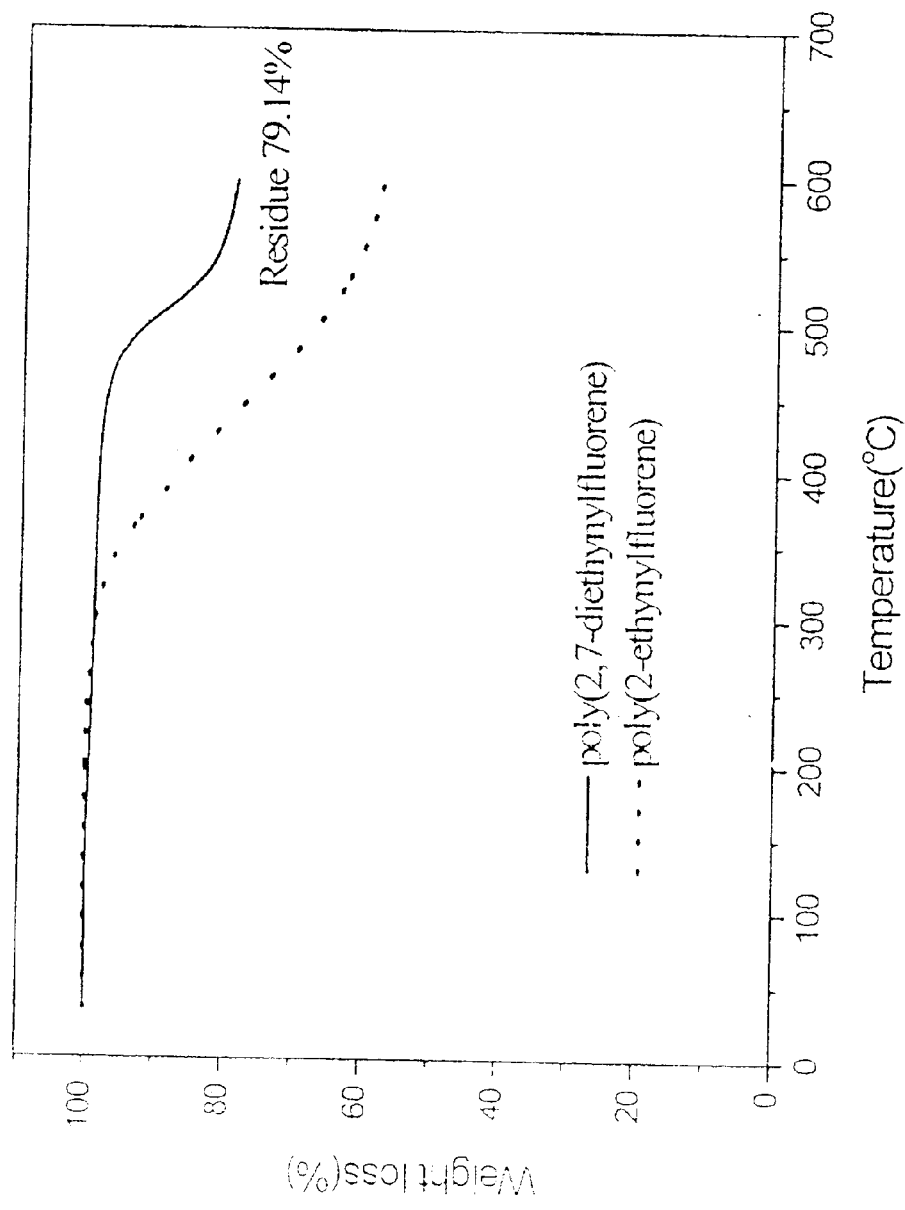
FIG. 5 represents TGA thermograms of 2-ethynylfluorene and 2,7-diethynylfluorene after thermal curing.

Thermal stability of 2-ethynylfluorene after thermal curing was examined by TGA analysis and the result was shown in FIG. 5. As shown in FIG. 5, a polymer prepared by polymerizing 2-ethynylfluorene by thermal curing at 230° C. under $N_2$ was stable up to 260° C.

EXAMPLE 2

Preparation of 2,7-DiethynylFluorene

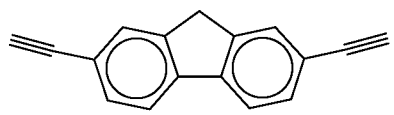 (2)

To 100 ml of propylene carbonate were added 10 g (0.06 mol) of fluorene and 22.43 g (0.126 mol) of N-bromosuccinimide (NBS). After the reaction mixture was stirred at 75° C. for 6 h, 200 ml of distilled water was added to obtain precipitate. The obtained precipitate was recrystallized from ethylacetate several times to give 10.89 g (56%) of 2,7-dibromofluorene.

Thereafter, to 150 ml of diisopropylamine were dissolved 10.89 g (336 mmol) of 2,7-dibromofluorene obtained above, 941 mg (0.67 mmol) of bis[triphenylphosphine]palladium dichloride, and 128 mg (0.67 mmol) of copper iodide. After the reaction mixture was stirred for 2 h at room temperature, 10.45 ml (73.9 mmol) of trimetlylsilyl acetylene was added dropwise to it. The reaction mixture was refluxed for 8 h and cooled. Solvent was removed under reduced pressure. The residue was extracted with benzene and the benzene layer was washed with distilled water. The washed benzene layer was concentrated to give 10.12 g(85%) of 2,7-di(trimethylsilylethynyl)fluorene.

Thereafter, 60 ml of 1N potassium hydroxide solution was slowly added to 10.12 g(28.2 mmol) of 2,7-di(trimethylsilylethynyl)fluorene dissolved in 150 mL of methanol. The reaction mixture was stirred for 3 h at room temperature and solvent was removed. Residue was extracted with ether and the ether layer was washed with distilled water. The washed ether layer was concentrated. The crude product was purified by column chromatography on silica gel by eluting with hexane/ethylacetate (15/1) to give 1.35 g (72%) of 2,7-diethynylfluorene of which mp was 125° C.

The DSC thermogram of 2,7-diethynylfluorene, as shown in FIG. 4, reveals that polymerization of 2,7-diethynylfluorene having two acetylene groups was started at around 198° C. It indicated that deposition on the substrate and polymerization of 2,7-diethynylfluorene can be simultaneously performed by controlling a temperature around 200° C.

Thermal stability of 2,7-diethynylfluorene after thermal curing was examined by TGA analysis as shown in FIG. 5. In FIG. 5 a polymer prepared by polymerizing 2,7-diethynylfluorene by thermal curing at 198° C. for 3 h under $N_2$ was stable up to 385° C.

EXPERIMENTAL EXAMPLE 1

Thermal Curing

Figure 6:
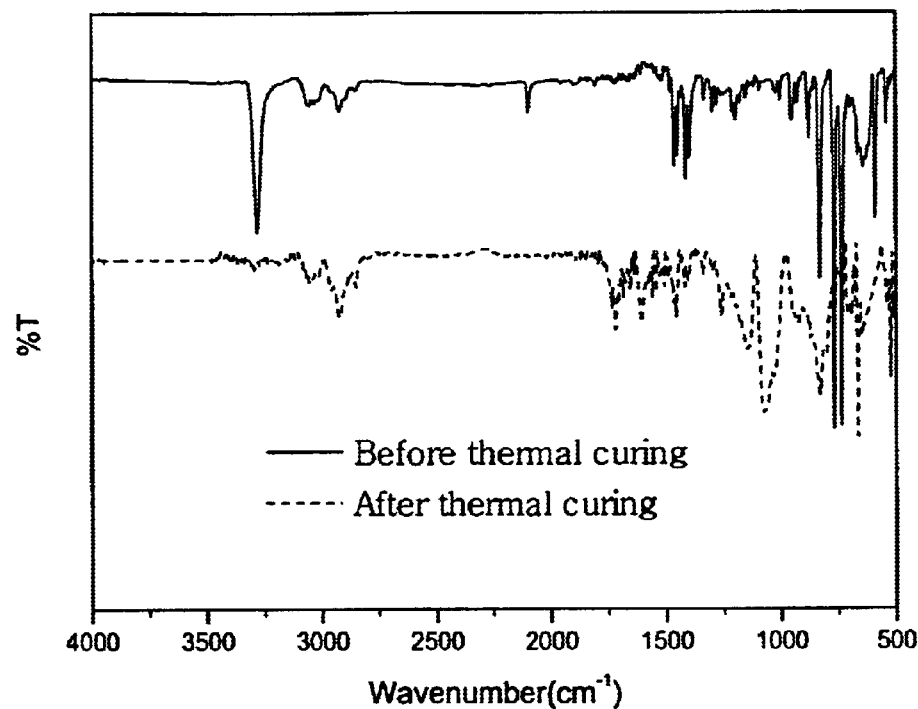
FIG. 6 represents IR spectra of 2-ethynylfluorene before and after thermal curing.
Figure 7:
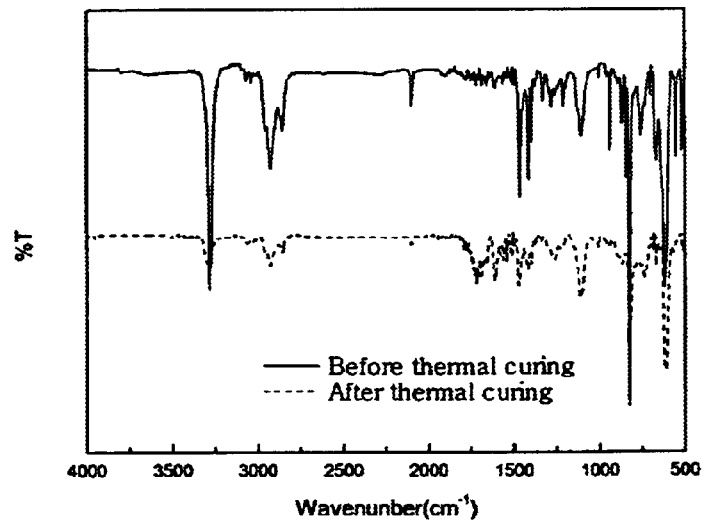
FIG. 7 represents IR spectra of 2,7-diethynylfluorene before and after thermal curing.

2-Ethynylfluorene prepared from Example 1 and 2,7-diethynylfluorene prepared from Example 2 were deposited on silicon wafer by vacuum deposition chamber of FIG. 1 in order to confirm by IR spectra whether those compounds having (an) acetylene group(s) were polymerized by heat treatment. During deposition, vacuum level was 2×10$^{-4}$ torr and deposited thickness was about 1500 Å. IR spectra of 2-ethynylfluorene and 2,7-diethynylfluorene before and after thermal curing under N$_2$ were examined and shown in FIGS. 6 and 7. Thermal curing of each 2-ethynylfluorene and 2,7-diethynylfluorene was carried out at 230° C. and at 198° C., respectively, for 30 min. In FIGS. 6 and 7, both 2-ethynylfluorene and 2,7-diethynylfluorene show strong peak of stretching vibration at 3283 cm$^{-1}$ for ≡C—H and a weak peak of stretching vibration at 2099 cm$^{-1}$ for C≡C before thermal curing. After thermal curing for 30 min, both stretching peaks for ≡C—H and C≡C were disappeared and a peak of stretching vibration at between 1600 and 1700 cm$^{-1}$ for C=C was appeared. This indicated that after thermal curing both 2-ethynylfluorene and 2,7-diethynylfluorene having (an) acetylene group(s) were polymerized by changing a triple bond, C≡C, to a double bond, C=C.

EXPERIMENTAL EXAMPLE 2

Figure 8:
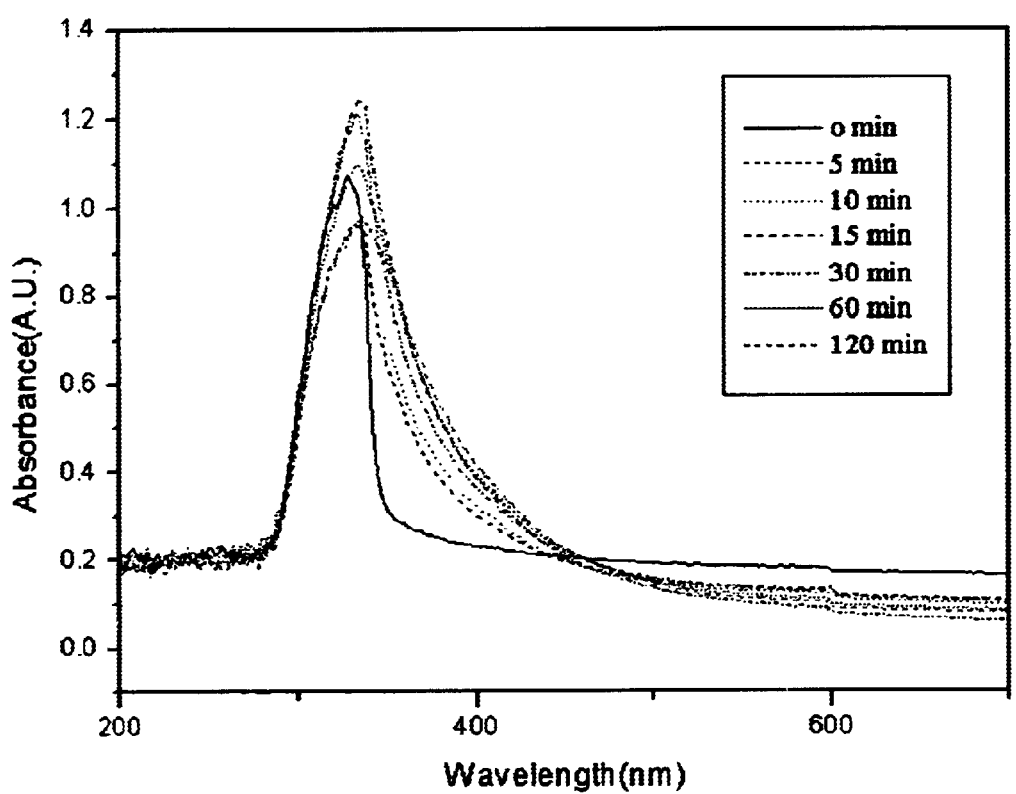
FIG. 8 represents changes of UV absorption spectra of 2,7-diethynylfluorene with UV irradiation.

Polymerization by UV Irradiation 2,7-Diethynylfluorene prepared from Example 2 was deposited on the glass using vacuum deposition chamber of FIG. 1, and was examined UV absorption spectrum during UV irradiation. During deposition, vacuum level was 2×10$^{-4}$ torr and deposited thickness was about 300 Å. FIG. 8 represents changes of UV absorption spectra at different irradiation time. As exposure of UV light increased, the width of maximum absorption peak at 340 nm was getting broader and the peak shifted toward longer wavelength. It indicated that the length of double bond was getting increased, that is, a triple bond of the compound having acetylene groups was changed into a double bond by polymerization with UV irradiation.

EXAMPLE 3

Preparation of Tri(4-ethynylphenyl)amine

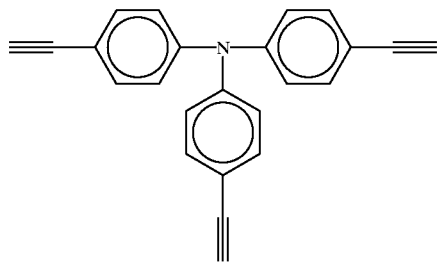

(3)

10 g (0.0408 mol) of triphenylamine was added to 150 ml of chloroform with stirring. 19.54 g (0.122 mol) of bromine dissolved in chloroform was added to the reaction mixture and stirred for 2 h at room temperature. 400 ml of hot ethanol was added to the reaction mixture and left at room temperature to produce precipitates. Said precipitates was extracted by methanol soxhlet to give 15.54 g (79%) of tri(4-bromophenyl)amine.

Thereafter, to 200 ml of diisopropylamine were added 15.54 g (0.032 mol of tri(4-bromophenyl)amine, 1.35 g (1.92 mmol) of bis[triphenylphosphin]palladium dichloride and 9.43 g (0.96 mmol) of copper iodide. After the reaction mixture was stirred for 2 h at room temperature, 9.43 g, (96 mmol) of trimethylsilyl acetylene was slowly added to the reaction mixture. The reaction mixture was refluxed for 8 h and cooled. Solvent was removed under the reduced pressure. The residue was extracted with benzene and the benzene layer was washed with distilled water. The washed benzene layer was concentrated to give 13.84 g (81%) of tri(4-trimethylsilylethynylphenyl)amine.

Figure 9:
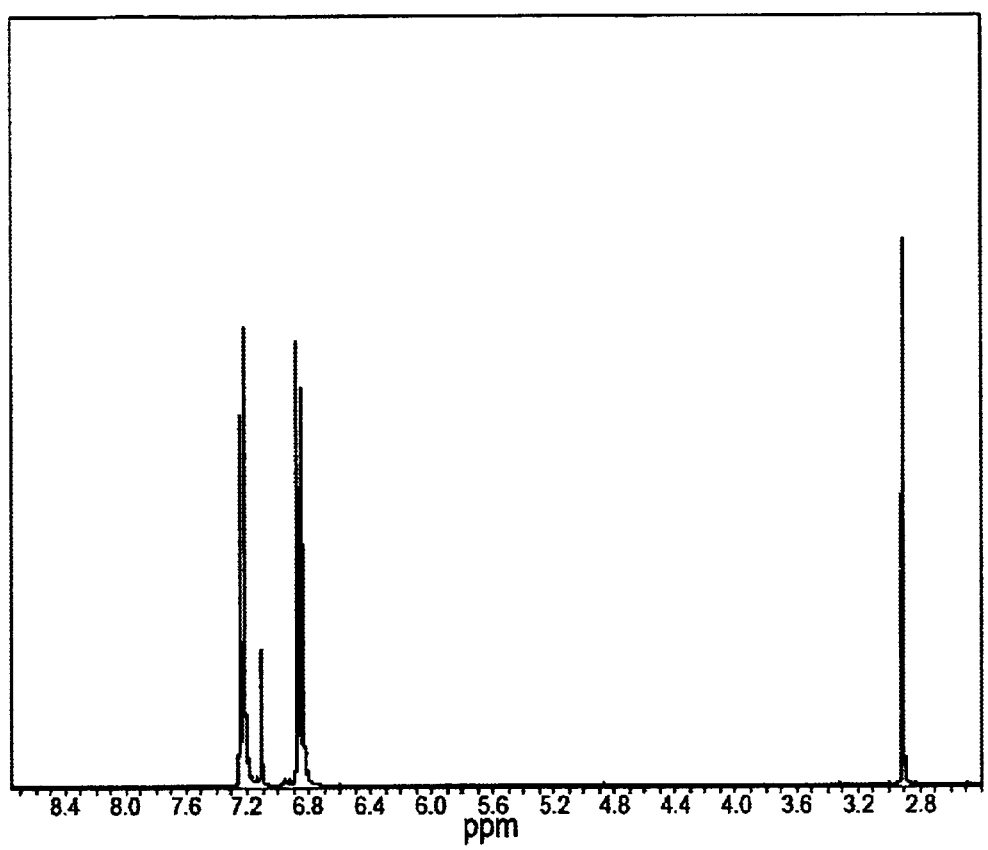
FIG. 9 represents NMR spectrum of tri(4-ethynylphenyl) amine.

To a mixture of 180 ml of tetrahydrofuran (THF) and 240 ml of methanol were added 13.84 g (0.026 mol) of tri(4-trimethylsilylethynylphenyl)amine and 4.53 g (0.078 mol) of potassium fluoride. The reaction mixture was heated at 50° C. for 5 h, cooled down to room temperature, and solvent was removed under the reduced pressure. The residue was extracted with ether and the ether layer was washed with distilled water. The washed ether layer was concentrated to give crude product. The crude product was purified by column chromatography on silica gel by eluting with hexane to give 6.182 g (75%) of tri(4-ethynylphenyl)amine of which NMR spectrum was shown in FIG. 9 and mp was 115° C.

Figure 10:
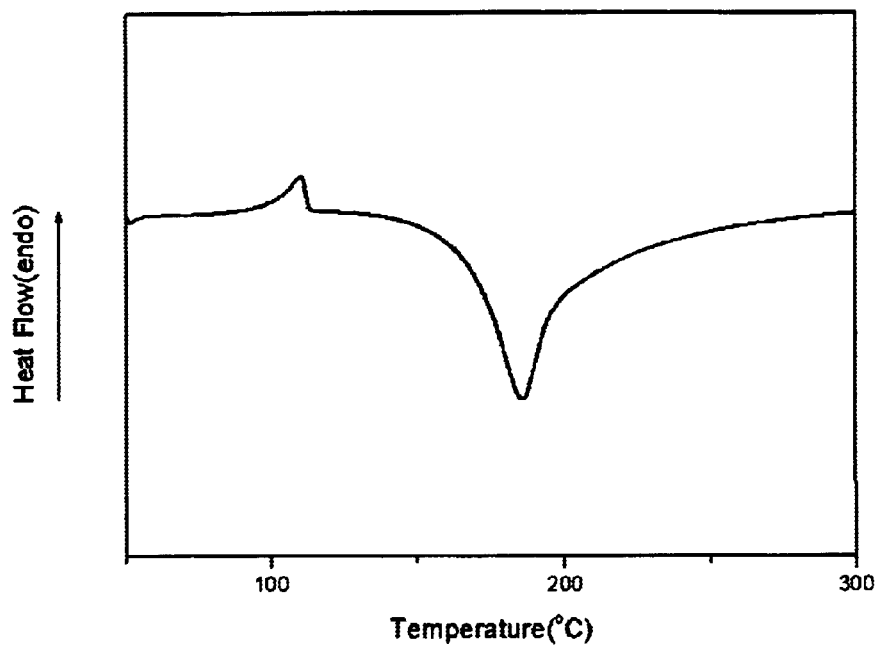
FIG. 10 represents DSC thermogram of tri(4-ethynylphenyl)amine.

The DSC thermogram of tri(4-ethynylphenyl)amine, as shown in FIG. 10, revealed that polymerization of tri(4-ethynylphenyl)amine having three acetylene groups was started at 185° C. It indicated that deposition on the substrate and polymerization of 2,7-diethynylfluorene can be simultaneously carried out by controlling a temperature around 185° C.

Figure 11:
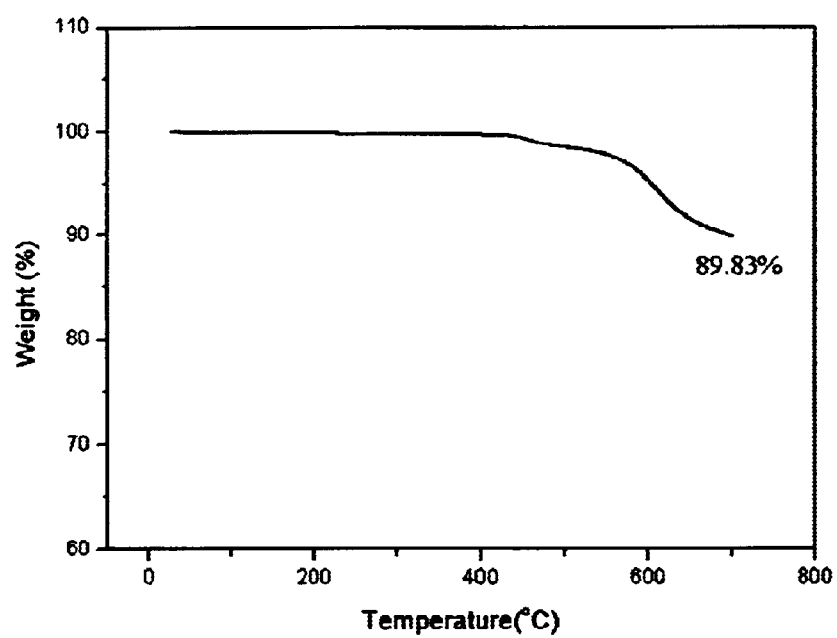
FIG. 11 represents TGA thermogram of tri(4-ethynylphenyl)amine after thermal curing.

Thermal stability of tri(4-ethynylphenyl)amine after thermal curing was examined by TGA analysis and the result was shown in FIG. 11. In FIG. 11 a polymer prepared by polymerizing tri(4-ethynylphenyl)amine by thermal curing at 185° C. under N$_2$ for 30 min was stable up to 375° C.

EXPERIMENTAL EXAMPLE 3

Polymerization by UV Irradiation

Figure 12:
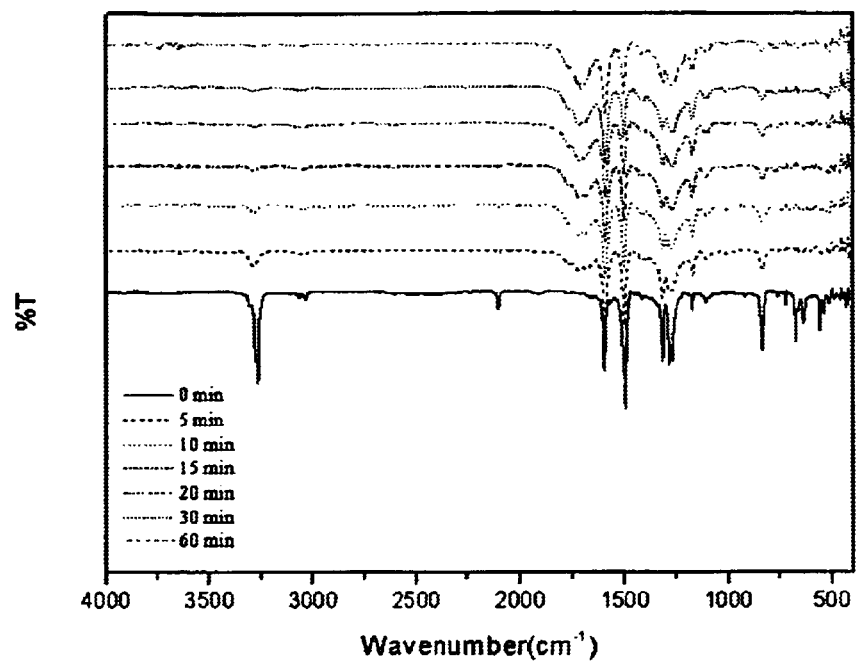
FIG. 12 represents changes of IR spectra of tri(4-ethynylphenyl)amine with UV irradiation.

Tri(4-ethynylphenyl)amine prepared from Example 3 was deposited on silicon wafer in the vacuum deposition chamber of FIG. 1 to examine by IR spectrum whether those compound having three acetylene groups was polymerized by UV irradiation. During deposition, vacuum level was 2×10$^{-3}$ torr and deposited thickness was about 1500 Å. IR spectra of tri(4-ethynylphenyl)amine FIG. 12, tri(4-ethynylphenyl)amine showed a strong peak of stretching vibration at 3277 cm$^{-1}$ for ≡C—H and a weak peak of stretching vibration at 2102 cm$^{-1}$ for C≡C before thermal curing. After thermal curing, both peaks for ≡C—H and C≡C were disappeared and a peak of stretching vibration at between 1600 and 1700 cm$^{-1}$ for C=C was appeared. This indicated that tri(4-ethynylphenyl) amine having three acetylene groups was polymerized with UV irradiation by changing a triple bond, C≡C, to a double bond, C=C.

Figure 13:
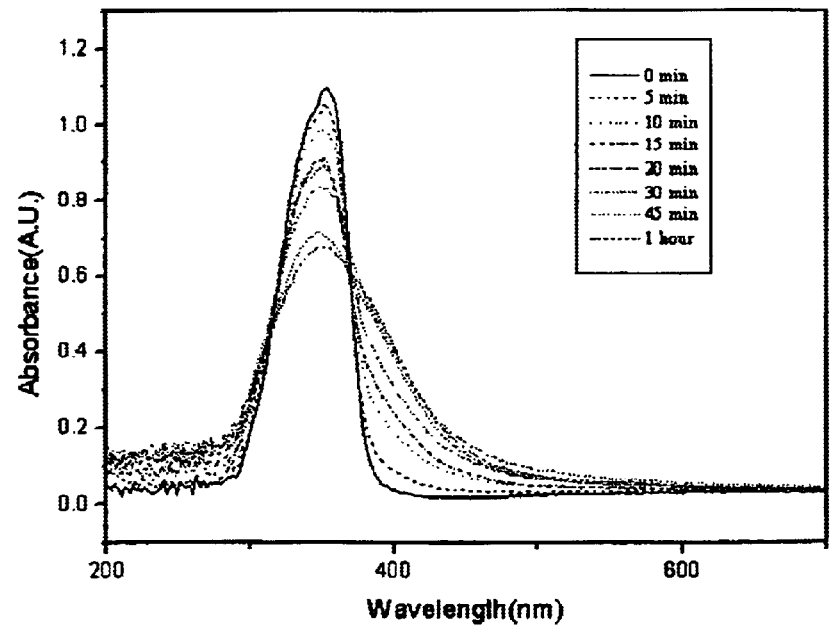
FIG. 13 represents changes of UV absorption spectra, tri(4-ethynylphenyl)amine with UV irradiation.

And polymerization of tri(4-ethynylphenyl)amine with UV light was also clarified by UV absorption spectrum. During deposition, vacuum level was 2×10$^{-4}$ torr and deposited thickness was about 300 Å. FIG. 13 showed changes of UV absorption spectra with irradiation time. As exposure time of UV light increased, the width of maximum absorption peat at 340 nm was getting broader and the peak was shifted toward longer wavelength. It indicated that the length of double bond was getting increased, that is, a triple boned of the compound having acetylene group was changed to a double bond by polymerization with UV light.

Figure 14:
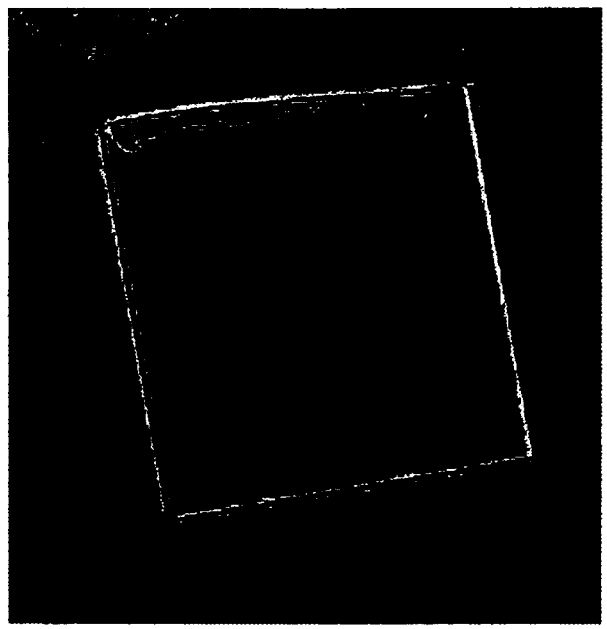
FIG. 14 represents picture of a pattern formed on the thin film of tri(4-ethynylphenyl)amine by UV irradiation through photomask.
Figure 15:
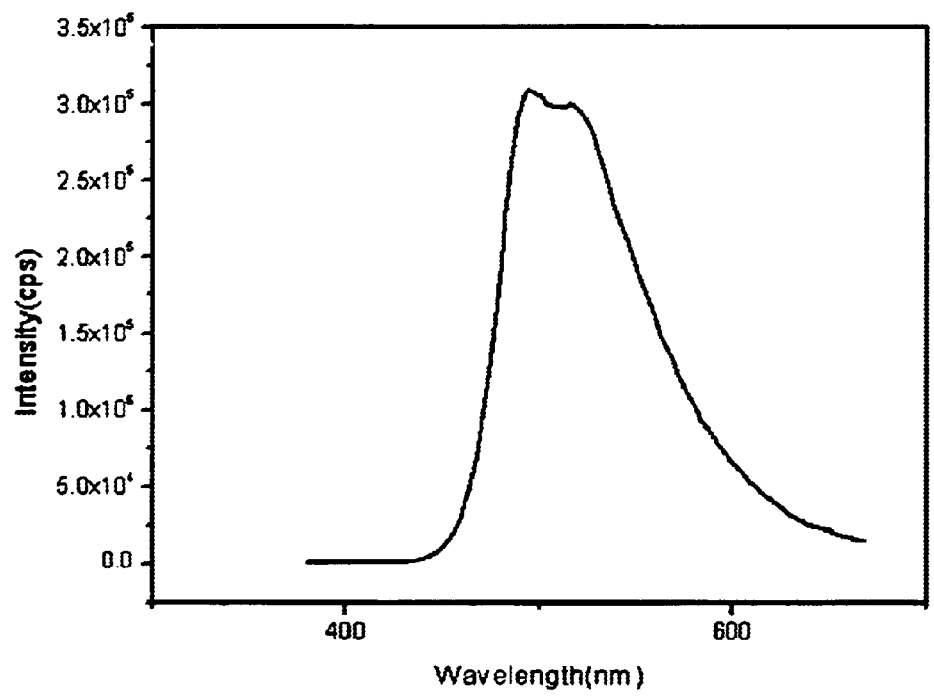
FIG. 15 represents electrophotoluminescene spectra from ITO/tri(4-ethynylphenyl)amine/Alq$_3$/Al device.

On the other hand, after exposing UV light at 254 nm or 320 nm of wavelength by using a mask on the substrate of the glass deposited with tri(4-ethynylphenyl)amine, a pattern was formed by dissolving the unexposed area in chloroform and the picture thereof was shown in FIG. 14. The compounds having acetylene groups can be cured by UV irradiation and a pattern thereof using a mask can be also formed. The organic compounds of the present invention can be used for preparing a thin film by vacuum deposition polymerization which is appropriate to negative-type photoresists.

EXAMPLE 4

Preparation of N,N-Bis(3-Methylphenyl)-N,N-(4-Ethynyl)Benzidine

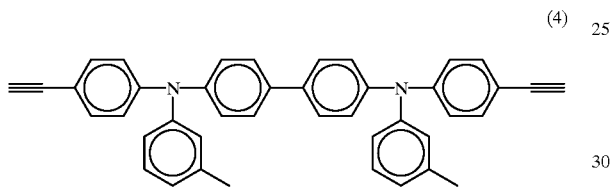

(4)

To 50 ml of diisopropylamine were added 3.3 g (4.89 mmol) of N,N-bis(3-methylphenyl)-N,N-di(4-bromophenyl)benzidine, 137 mg (0.196 mmol) of bis[triphenylphosphine]palladium dichloride and 18.7 mg (0.098 mmol) of copper iodide. After the reaction mixture was stirred for 2 h at room temperature, 0.96 mg (9.78 mmol) of trimethylsilylacetylene was slowly added to it. The reaction mixture was refluxed for 8 h. The solvent was removed under the reduced pressure. The residue was extracted with benzene and the benzene layer was washed with distilled water. The washed benzene layer was concentrated to dryness to give 2.705 g (78%) of N,N-bis(3-methylphenyl)-N,N-di(4-trimethylsilylethynylphenyl) benzidine.

To a mixture of 60 ml of THF and 80 ml of methanol were dissolved 2.705 g (3.814 mmol) of N,N-bis(3-methylphenyl)-di(4-trimethylsilylethynylphenyl)benzidine and 0.443 g (7/628 mmol) of KF. After the reaction mixture was stirred for 5 h at 50° C., it was cooled to room temperature and the solvent was removed to dryness. The residue was extracted with chloroform and the chloroform layer was washed with distilled water. The washed chloroform layer was concentrated to dryness to give crude Product which was further purified by column chromatography on silica gel by eluting with hexane/ethylacetate (9/1) to give 1.852 g (86%) of N,N-bis(3-methylphenyl)-N,N-di(4-ethynylphenyl)benzidine.

TABLE 1

Elemental Analysis of N,N-bis(3-methylphenyl)-N,N-di(4-ethynylphenyl)benzidine

|  | C | H | N |
|---|---|---|---|
| Found | 89.27% | 5.77% | 4.94% |
| Calculated | 89.33% | 5.71% | 4.96% |

EXAMPLE 5

Preparation of (4-ethynyl)diphenylamine

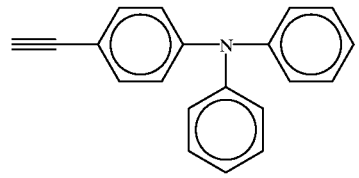

(5)

1.503 g (71%) of 4-(ethynylphenyl)diphnylamine was prepared by the same procedure of Example 4 with using 3.0 g (9.25 mmol) of (4-bromophenyl)diphenylamine(4-bromophenyl)diphenylamine instead of N,N'-bis(3-methylphenyl)-N,N'-di(4-bromophenyl)benzidine.

TABLE 2

Elemental Analysis of 4-(ethynylphenyl)diphenylamine

|  | C | H | N |
|---|---|---|---|
| Found | 89.16% | 5.70% | 5.14% |
| Calculated | 89.19% | 5.61% | 5.20% |

EXAMPLE 6

Preparation of 1,3-di(5-(4-ethynylphenyl)-1,3,4-oxadiazole)benzene

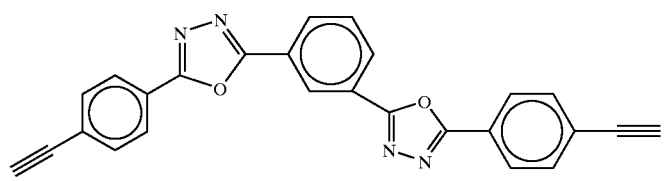

(6)

1.75 g (65%) of 1,3-di(5-(4-ethynylphenyl)-1,3,4-oxadiazole)benzene was prepared by the same procedure of Example 4 with using 5.0 g (9.54 mmol) of 1,3-di(5-(4-bromophenyl)-1,3,4-oxadiazole)benzene instead of N,N'-bis(3-methylphenyl)-N,N'-di(4-bromophenyl)benzidine.

TABLE 3

Elemental Analysis of 1,3-di(5-(4-ethynylphenyl)-1,3,4-oxadiazole)benzene

|  | C | H | N |
|---|---|---|---|
| Found | 75.29% | 3.44% | 13.49% |
| Calculated | 76.65% | 3.41% | 13.52% |

EXAMPLE 7

Preparation of 5,5-Diethynyl-2,2:5,2-Terthiophene

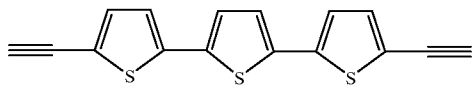
(7)

2.37 g (65%) of 5,5-diethynyl-2,2:5,2-terthiophene was prepared by the same procedure of Example 4 with using 5.0 g (12.3 mmol) of 5,5-dibromo-2,2:5,2-terthiophene instead of N,N'-bis(3-methylphenyl)-N,N'-di(4-bromophenyl)benzidine.

TABLE 4

Elemental Analysis of 5,5-diethynyl-2,2:5,2-terthiophene

|  | C | H |
|---|---|---|
| Found | 64.8% | 2.76% |
| Calculated | 64.83% | 2.72% |

EXAMPLE 8

Preparation of 9,10-diethynylanthracene

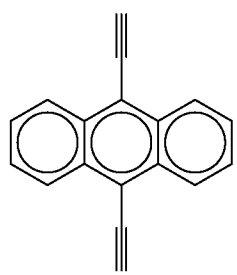
(8)

2.42 g (72%) of 9,10-diethynylanthracene was prepared by the same procedure of Example 4 with using 5.0 g (14.9 mmol) of 9,10-dibromoanthracene instead of N,N'-bis(3-methylphenyl)-N,N'-di(4-bromophenyl)benzidine.

TABLE 5

Elemental Analysis of 9,10-diethynylanthracene

|  | C | H |
|---|---|---|
| Found | 95.53% | 4.47% |
| Calculated | 95.55% | 4.45% |

EXAMPLE 9

Preparation of 1,4-Di(4-ethynylphenyl)adamantine

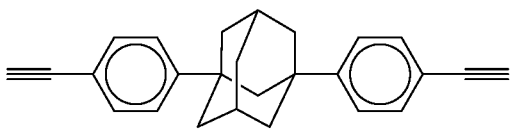
(9)

2.63 g (70%) of 1,4-di(4-ethynylphenyl)adamantine was prepared by the same procedure of Example 4 with using 5 0g (14.9mmol) of 1,4-di(4-bromophenyl)adamantine, prepared by reacting 5.0 g (21.9 mmol) of 1,4-diphenyladamantane and bromine, instead of N,N'-bis(3-methylphenyl)-N,N'-di(4-bromophenyl)benzidine.

TABLE 6

Elemental Analysis of 1,4-di(4-ethynylphenyl)adamantine

|  | C | H |
|---|---|---|
| Found | 92.78% | 7.22% |
| Calculated | 92.81% | 7.19% |

EXAMPLE 10

Electroluminescence device was fabricated by using a thin film formed by means of vacuum deposition polymerization of tri(4-ethynylphenyl)amine prepared from Example 3 as a hole transport layer and tris(8-hydroxyquinolinato)aluminum (Alq$_3$) as an emission layer. ITO glass electrode was placed into a mixture of acetone and isopropyl alcohol and washed several times with ultrasonic cleaner. Tri(4-ethynylphenyl)amine was deposited on the ITO electrode by a deposition chamber of FIG. 1 under 2.0×10$^{-5}$ torr of vacuum level and with 0.5 Å/sec of rate to form a thin film having 80 Å of thickness. During deposition, a hole transport layer was prepared by polymerizing a monomer of tri(4-ethynylphenyl)amine with UV irradiation. After polymerization, an emission layer having 500 Å of thickness was formed by depositing Alq$_3$ on the hole transport layer with a deposition chamber under 2.0×10$^{-5}$ torr of vacuum level and with 2.0 Å/sec of rate. Thereafter, aluminum was deposited on the emission layer with a deposition chamber under 2.0×10$^{-5}$ torr of vacuum level and with 5.0 Å/sec of rate to form a metal electrode layer having 1,500 Å of thickness. FIG. 5 showed an electroluminescence spectra of ITO/tri(4-ethynylphenyl)amine/Alq$_3$/Al electroluminescence device. Said ITO was connected with anode and said Al electrode was connected with cathode and also an operating voltage was 3.5V and an electric current was 0.5 mA.

As described above in detail, the present invention provides an organic thin film of an organic compound having at least one acetylene group formed by deposition under the vacuum and simultaneous or then polymerization by heat treatment or UV irradiation. The process of the present invention does not require high temperature process and does not produce by-products. The thin film formed by vacuum deposition polymerization has uniform thickness and excellent thermal stability and further, be applied in various fields such as interlayer dielectric film of semiconductors, electroluminescence devices, solar cells, drum of copy machine and laser printer, and various sensors.

What is claimed is:

1. A vacuum deposition polymerization method in which at least one organic compound having an acetylene group is deposited on a substrate and simultaneously or then polymerized by heat treatment and/or UV irradiation to form a polymer thin film wherein said organic compound is expressed by formula 1, $$[R_1 \!-\!\!\equiv\!\!-\! R_2]_n\!-\!R \qquad (1)$$

wherein $R_1$ is a hydrogen atom; $R_2$ is a bond or

n is a natural number of 1 or above; and R is selected from the group consisting of:

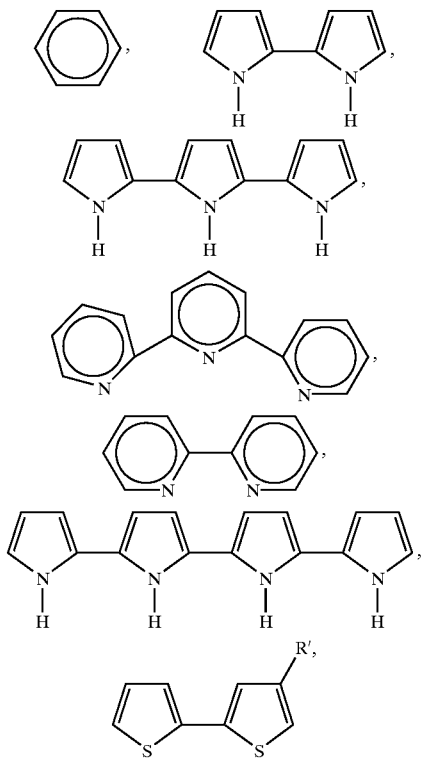

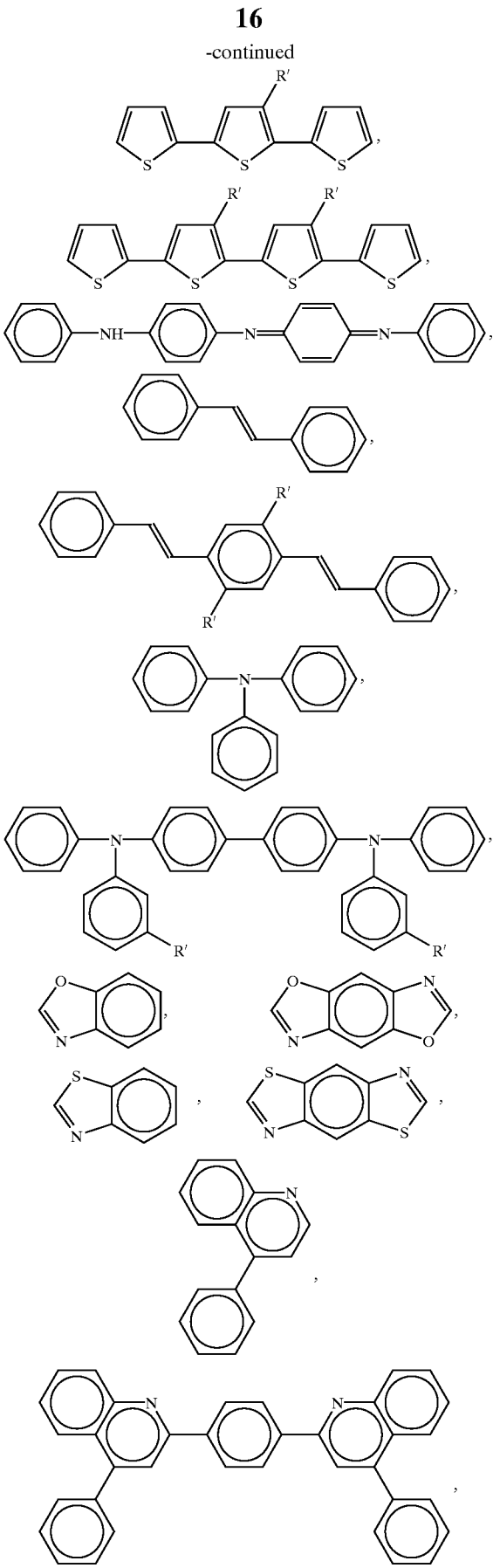

-continued

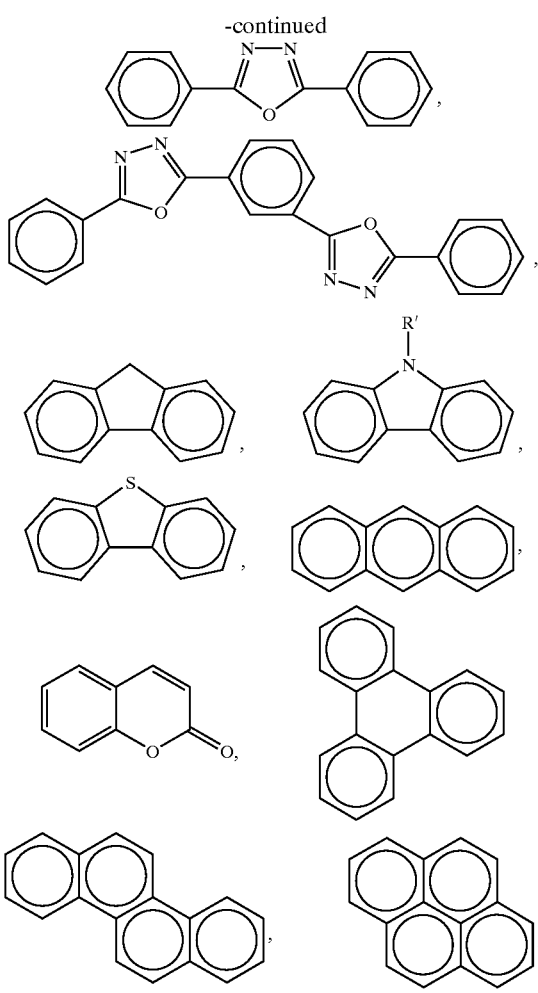

-continued

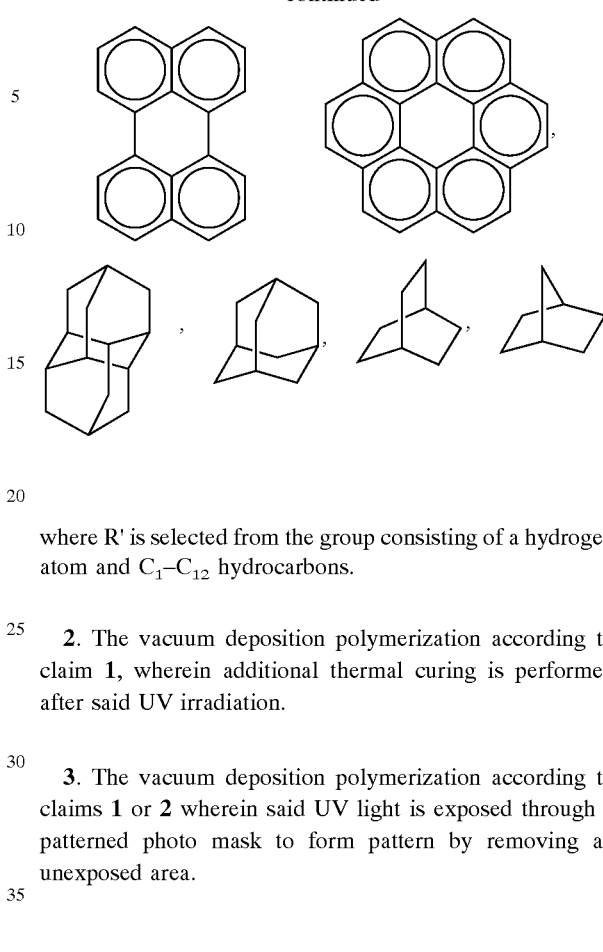

where R' is selected from the group consisting of a hydrogen atom and $C_1$–$C_{12}$ hydrocarbons.

2. The vacuum deposition polymerization according to claim 1, wherein additional thermal curing is performed after said UV irradiation.

3. The vacuum deposition polymerization according to claims 1 or 2 wherein said UV light is exposed through a patterned photo mask to form pattern by removing an unexposed area.

* * * * *